United States Patent [19]

Costales et al.

[11] Patent Number: 5,201,938
[45] Date of Patent: Apr. 13, 1993

[54] N-PYRAZOLYL-1,2,4-TRIAZOLO[1,5-C]PYRIMIDINE-2-SULFONAMIDE HERBICIDES

[75] Inventors: Mark J. Costales; John C. Van Heertum, both of Concord, Calif.; William A. Kleschick, Indianapolis, Ind.; Robert J. Ehr, Vallejo; Patricia G. Ray, Walnut Creek, both of Calif.

[73] Assignee: DowElanco, Indianapolis, Ind.

[21] Appl. No.: 733,048

[22] Filed: Jul. 19, 1991

[51] Int. Cl.$^5$ .................... A01N 43/54; C07D 487/04
[52] U.S. Cl. .................... 504/241; 544/263; 548/371.4; 548/372.5; 548/371.7
[58] Field of Search ..................... 544/263; 71/92

[56] References Cited

U.S. PATENT DOCUMENTS

| | | | |
|---|---|---|---|
| 4,921,527 | 1/1990 | Tseng | 544/263 |
| 4,954,163 | 9/1990 | Kleschick et al. | 71/92 |
| 5,010,195 | 4/1991 | Van Heertum et al. | 544/263 |
| 5,013,351 | 5/1991 | Jelich et al. | 71/92 |

FOREIGN PATENT DOCUMENTS

| | | | |
|---|---|---|---|
| 951652 | 3/1964 | European Pat. Off. | 544/263 |
| 244948 | 11/1987 | European Pat. Off. | |
| 0419831 | 4/1991 | European Pat. Off. | 403/4 |

*Primary Examiner*—Donald G. Daus
*Attorney, Agent, or Firm*—D. Wendell Osborne

[57] ABSTRACT

N-(3-, 4-, and 5-)-pyrazolyl-1,2,4-triazolo[1,5-c]pyrimidine-2-sulfonamide compounds, substituted on the pyrimidine ring with an alkoxy group and on the pyrazine ring, such as N-(4-bromo-1-methylpyrazol-3-yl)-7-chloro-5-methoxy-1,2,4-triazolo[1,5-c]pyrimidine-2-sulfonamide, were prepared from alkoxy substituted 1,2,4-triazolo[1,5-c]-pyrimidine-2-sulfonyl halides by condensation with substituted (3-, 4-, and 5-aminopyrazoles in the presence of a pyridine base and a catalytic amount of dimethyl sulfoxide. The compounds were found to possess general and, in some cases, selective pre- and postemergence herbicidal activity.

40 Claims, No Drawings

N-PYRAZOLYL-1,2,4-TRIAZOLO[1,5-C]PYRIMIDINE-2-SULFONAMIDE HERBICIDES

BACKGROUND OF THE INVENTION

The present invention relates to novel substituted N-pyrazolyl-1,2,4-triazolo[1,5-c]-pyrimidine-2-sulfonamide compounds, to herbicidal compositions containing the compounds, and to the utility of the compounds for the control of unwanted vegetation.

The control of unwanted vegetation by means of chemical agents, i.e., herbicides, is an important aspect of modern agriculture and land management. While many chemicals that are useful in unwanted vegetation control are known, new compounds that are more effective generally or for specific plant species, are less damaging to desirable vegetation, are safer to man or the environment, are less expensive to use, or have other advantageous attributes are desirable.

Certain substituted 1,2,4-triazolo[1,5-a]-pyrimidine-2-sulfonamide compounds are known and are known to possess herbicidal activity (U.S. Pat. No. 4,954,163). In addition, certain N-aryl-1,2,4-triazolo[1,5-c]pyrimidine-2-sulfonamide compounds (European Application 244948) and certain alkoxy-substituted N-(substituted-phenyl)-1,2,4-triazolo-[1,5-c]pyrimidine-2-sulfonamide compounds (U.S. Pat. No. 5,010,195) and their herbicidal utility have been disclosed.

SUMMARY OF THE INVENTION

It has now been found that N-pyrazolyl-1,2,4-triazolo[1,5-c]pyrimidine-2-sulfonamide compounds of the formula:

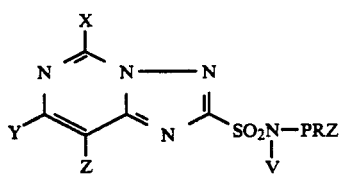

Formula I wherein
X represents H, OR, $R^2$, or SR; and
Y and Z each, independently represent H, OR, $CH_2OCH_3$, $R^2$, F, Cl, Br, or I;
with the proviso that at least one of X, Y, and Z represents OR:
V represents H or $C(O)R^2$ and when V represents H, the agriculturally acceptable salts thereof:
PRZ represents

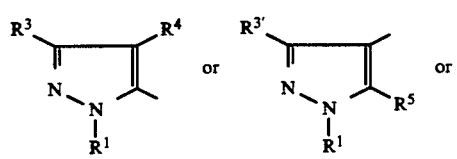

5-Pyrazolyl    4-Pyrazolyl

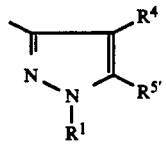

3-Pyrazolyl

R represents $(C_1-C_3)$alkyl;
$R^1$ represents $CH_3$, $COCH_3$, $CO_2R$, $CONR_2$, or pyridinyl or phenyl each optionally substituted with up to two substituents selected from $CH_3$, $CF_3$, F, Cl, Br, $OCH_3$, and $SCH_3$;
$R^2$ represents $(C_1-C_3)$alkyl optionally singly to completely substituted with F;
$R^3$ and $R^{5'}$ each independently represent H, $R^2$, F, Cl, Br, or I;
$R^{3'}$ and $R^5$ each independently represent H, $R^2$, F, Cl, Br, I, $NO_2$, $COR^2$, $CO_2R$, or phenyl optionally substituted with up to two substituents selected from $CH_3$, $CF_3$, F, Cl, Br, $OCH_3$, and $SCH_3$; and
$R^4$ represents F, Cl, Br, I, $R^2$, $SR^2$, $NR_2$, $COR^2$, $SO_2R^2$, COphenyl, or phenyl, each phenyl optionally substituted with up to two substituents selected from $CH_3$, $CF_3$, F, Cl, Br, $OCH_3$, and $SCH_3$ are useful in the control of unwanted vegetation and in many cases can be employed in the presence of valuable crops. The compounds are herbicidally effective against a wide variety of both broadleaf and grassy weeds and are especially useful for industrial weed control. The compounds of Formula I, usually in the form of an herbicidal composition containing one or more of them in admixture with an agriculturally acceptable adjuvant or carrier, exhibit herbicidal properties when applied either directly to the unwanted vegetation or to the locus thereof and when applied either preemergence or postemergence.

DETAILED DESCRIPTION OF THE INVENTION

The compounds of the present invention include substituted N-(3-, 4-, and 5-)pyrazolyl-1,2,4-triazolo[1,5-c]pyrimidine-2-sulfonamides of Formula I wherein, in the pyrimidine ring, the substituent X represents H, OR, $R^2$, or R and the substituents Y and Z each, independently represent H, OR, $CH_2OCH_3$, $R^2$, F, Cl, Br, or I, with the proviso that at least one of X, Y, and Z represents OR (wherein R represents $(C_1-C_3)$alkyl): in the sulfonamide linking moiety, V represents H or an agriculturally acceptable salt derived therefrom or $C(O)R^2$ (wherein $R^2$ represents $(C_1-C_3)$alkyl optionally singly to completely substituted with F); and the moiety PRZ represents

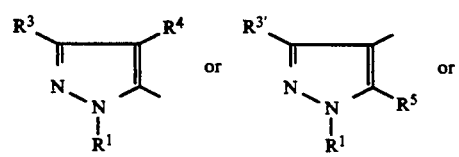

5-Pyrazolyl    4-Pyrazolyl

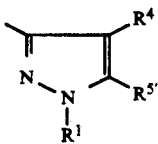

3-Pyrazolyl wherein, of the substituent groups, R¹ represents CH₃, COCH₃, CO₂R, CONR₂, or pyridinyl or phenyl each optionally substituted with up to two substituents selected from CH₃, CF₃, F, Cl, Br, OCH₃, and SCH₃; R³ and R⁵′ represent H, R², F, Cl, Br, or I: R³′ and R⁵ each independently represent H, R², F, Cl, Br, I, NO₂, COR², CO₂R, or phenyl optionally substituted with up to two substituents selected from CH₃, CF₃, F, Cl, Br, OCH₃, and SCH₃; and R⁴ represents F, Cl, Br, I, R², SR², NR₂, COR², SO₂R², COphenyl, or phenyl, each phenyl optionally substituted with up to two substituents selected from CH₃, CF₃, F, Cl, Br, OCH₃, and SCH₃. Each of these compounds is a substituted N-(3-, 4- or 5-)pyrazolyl-1,2,4-triazolo[1,5-c]-pyrimidine-2-sulfonamide compound possessing at least one alkoxy substituent on the pyrimidine ring and at least one substituent on the pyrazole ring.

While each of the 1,2,4-triazolo[1,5-c]-pyrimidine-2-sulfonamide compounds described by Formula I is within the scope of the invention, the degree of herbicidal activity and the spectrum of weed control obtained varies depending upon the substituents present and, consequently, certain of the compounds are preferred. Compounds of Formula I wherein at least one of X, Y, and Z represents methoxy or ethoxy (R of OR represents methyl or ethyl) are usually preferred. Compounds wherein X represents methoxy or ethoxy are usually more preferred. Compounds wherein X represents methoxy or ethoxy and one of Y and Z represents hydrogen and the other represents OCH₃, OC₂H₅, CH₃, F, Cl, Br, or I are sometimes most preferred. Compounds of Formula I wherein PRZ represents a substituted 3-pyrazolyl or a 5-pyrazolyl moiety are often preferred. Compounds of Formula I wherein, in the PRZ moiety, R¹ represents CH₃ are usually preferred. When PRZ represents a substituted 3-pyrazolyl moiety, it is typically preferred that R⁴ represents Cl, Br, I, or CF₃ and R⁵′ represents H: when PRZ represents a substituted 4-pyrazolyl moiety, it is typically preferred that R³′ represents Cl, Br, I, or CF₃ and R⁵ represents H, Cl, Br, I, or CF₃; and when PRZ represents a substituted 5-pyrazolyl moiety, it is typically preferred that R³ represents H and R⁴ represents Cl, Br, I, or CF₃. Compounds of Formula I wherein V represents hydrogen and the agriculturally acceptable salts derived therefrom are normally preferred as well. Some of the specifically preferred compounds of the invention include the following: N-(4-bromo-1-methyl-3-pyrazolyl)-7-chloro-5-methoxy-1,2,4-triazolo[1,5-c]-pyrimidine-2-sulfonamide, N-(4-iodo-1-methyl-3-pyrazolyl)-7-chloro-5-methoxy-1,2,4-triazolo[1,5-c]-pyrimidine-2-sulfonamide, N-(4-bromo-1-methyl-3-pyrazolyl)-5-methoxy-7-methyl-1,2,4-triazolo[1,5-c]-pyrimidine-2-sulfonamide, N-(4-bromo-1-methyl-3-pyrazolyl)-5-ethoxy-7-methyl-1,2,4-triazolo[1,5-c]-pyrimidine-2-sulfonamide, N-(4-bromo-1-methyl-3-pyrazolyl)-8-chloro-5-methoxy-1,2,4-triazolo[1,5-c]-pyrimidine-2-sulfonamide, N-(4-bromo-1-methyl-3-pyrazolyl)-5-ethoxy-1,2,4-triazolo[1,5-c]pyrimidine-2-sulfonamide and N-(4-bromo-1-methyl-5-pyrazolyl)-7-fluoro-5-ethoxy-1,2,4-triazolo[1,5-c]pyrimidine-2-sulfonamide.

The term alkyl as used herein includes straight chain and branched chain moieties. Thus, typical alkyl groups are methyl, ethyl, 1-methylethyl, and propyl. Methyl is often preferred. Typical alkyl singly to completely substituted with fluorine groups include trifluoromethyl, monofluoromethyl, 2,2,2-trifluoroethyl, 2,3-difluoropropyl, and the like; trifluoromethyl is often preferred.

A listing of some typical compounds of the invention is given in Table 1.

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula

R⁶R⁷R⁸NH⊕ wherein R⁶, R⁷, and R⁸ each, independently represents hydrogen or C₁-C₁₂ alkyl, C₃-C₁₂ cycloalkyl, or C₃-C₁₂ alkenyl, each of which is optionally substituted by one or more hydroxy, C₁-C₈ alkoxy, C₁-C₈ alkylthio or phenyl groups; provided that R⁶, R⁷, and R⁸ are sterically compatible. Additionally, any two of R⁶, R⁷, and R⁸ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine. In the case of metal hydroxides, it is important not to use a large excess of the base as compounds of Formula I are not stable in highly alkaline media. Amounts close to the stoichiometric quantities are preferred.

The compounds of Formula I wherein V represents hydrogen can generally be prepared by combining a 1,2,4-triazolo1,5-c]pyrimidine-2-sulfonyl halide compound of Formula II with an appropriately substituted aminopyrazole compound of Formula III (a 5-aminopyrazole), Formula IV (a 4-aminopyrazole), or Formula V (a 3-aminopyrazole) in the presence of pyridine or a methylpyridine compound, and, optionally but preferably, a catalytic amount of dimethyl sulfoxide. The substituents X, Y, and Z of Formula II and R¹, R³, R³′, R⁴, R⁵, and R⁵′ of Formulas III, IV, and V are as defined in the Summary of the Invention: the substituent G of Formula II is chloro or bromo.

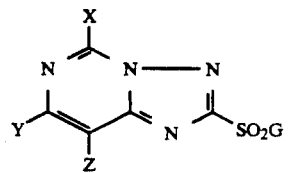

Formula II

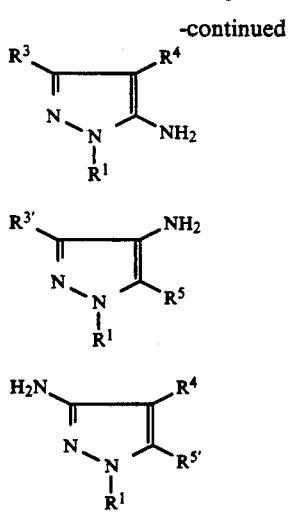

Formula III

Formula IV

Formula V

The preparation is usually accomplished by placing the 1,2,4-triazolo[1,5-c]pyrimidine-2-sulfonyl halide, preferably chloride, of Formula II, the aminopyrazole, and an inert solvent, such as acetonitrile, N,N-dimethylformamide, N-methyl-2-pyrrolidinone, tetrahydrofuran, and the like, in a vessel and then adding the pyridine or methylpyridine, preferably pyridine, and the catalytic amount of dimethyl sulfoxide. The mixture is allowed to react, typically at ambient temperature, but heating if necessary. After a substantial quantity of the compound of Formula I has formed or a substantial quantity of the sulfonyl halide of Formula II has been consumed, the desired product is recovered, typically removing the solvent by evaporation, adding water, and removing the liquids from the solid that forms by filtration or centrifugation. The product recovered can be purified, if desired, by extracting with an immiscible organic solvent, such as methylene chloride, and with water. Alternatively, the desired compounds of Formula I can be purified by recrystallization and by other commonly used methods.

Approximately equimolar quantities of the compounds of Formulas II and III, IV, or V are generally used in the preparation of compounds of Formula I although a substantial excess of one or the other may be employed. The pyridine compound is generally employed in an amount of from at least 1 to about 5 moles per mole of compound of Formula II. Dimethyl sulfoxide is typically used in less than an equimolar amount; amounts over about 0.5 mole per mole of compound of Formula II are usually deleterious. Acetonitrile is often the preferred solvent.

It is sometimes advantageous to prepare the compounds of Formula I by condensing a compound of Formula II with an N-trialkylsilyl derivative of a substituted (3-, 4-, or 5-)aminopyrazole compound. The method employed is analogous to that described in U.S. Pat. No. 4,910,306 for N-trialkylsilylanilines. The reaction conditions required are essentially the same as those described hereinabove for the condensation of a compound of Formula II with a substituted aminopyrazole with the exception that the pyridine compound base may be omitted. The substituted N-trialkylsilylaminopyrazole compounds employed can be prepared from the corresponding substituted aminopyrazole compounds by treatment with a trialkylsilyl halide and a trialkylamine as described in U.S. Pat. No. 4,910,306 for aniline compounds. Sodium iodide is typically employed as a catalyst when the halide is chloride. The N-trialkylsilylaminopyrazole compounds are typically prepared and used immediately and without purification.

Compounds of Formula I wherein V represents hydrogen and X and/or Y represents $SCH_3$ or OR, can be made from the corresponding compounds of Formula I wherein X and/or Y represents Cl by treatment with an appropriate nucleophilic reagent, such as sodium methoxide or sodium methanethiolate in methanol. The reaction conditions employed are similar to those used for the related exchange reactions of 2- and 4-chloropyrimidines. Non-aqueous media are preferred. Selective replacement of chlorine in the X position can readily be achieved as this chlorine is much more reactive than chlorine in the Y position.

Compounds of Formula I wherein V represents $C(O)R^2$ can be prepared from compounds of Formula I wherein V represents hydrogen by acylation with a compound of the formula $R^2C(O)Cl$ using conventional procedures known in the art for the acylation of sulfonamides.

The 1,2,4-triazolo[1,5-c]pyrimidine-2-sulfonyl halide compounds of Formula II and their analogs wherein X represents chloro can be prepared by the methods taught in U.S. Pat. No. 5,010,195.

The substituted 3-, 4-, and 5-aminopyrazoles that are required as intermediates for the compounds of Formula I are known in the art or can be prepared by the general methods known in the art or provided herein.

While it is possible to utilize the 1,2,4-triazolo[1,5-c]pyrimidine-2-sulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate: soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate: sorbitol esters, such as sorbitol oleate; quaternary amines, such as lauryl trimethylammonium chloride: polyethylene glycol esters of fatty acids, such as polyethylene glycol stearate: block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence and postemergence herbicides. They are especially useful for the non-selective control of undesirable vegetation. Some of the compounds, however, are useful for the selective control of broadleaf plants and nutsedge in grass crops, such as corn, wheat, barley, and rice. The selective control of weeds growing in paddy rice is of particular interest. Compounds of Formula I wherein the substituents in the pyrazole ring are as follows are usually preferred: $R^1$ represents $CH_3$; $R^3$, $R^{3'}$, $R^5$, and $R^{5'}$ each independently represent H, F, Cl, Br, or I; and $R^4$ represents F, Cl, Br, or I. Compounds of Formula I wherein X represents $OCH_3$ or $OC_2H_5$, Y represents $CH_3$ or $C_2H_5$, and Z represents H are also often preferred. Other of the compounds can be used to control broadleaf weeds in soybeans and cotton. Examples of the types of broadleaf weeds controlled include various species of prickly sida, morning glory, cocklebur, jimsonweed, velvet leaf, pigweed and black nightshade. Certain grassy weeds, such as crabgrass, barnyard grass, and yellow foxtail are also often controlled. As will be appreciated by those skilled in the art, not all of the compounds control all of the weeds or are selective for all of the crops.

The term herbicide is used herein to mean an active ingredient which controls or adversely modifies the growth of plants. An herbicidally effective or vegetation controlling amount is an amount of active ingredient which causes an adversely modifying effect and includes deviations from natural development, killing, regulation, dessication, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote selective herbicidal action. Generally, it is preferred to apply the compounds of Formula I postemergence to relatively immature plants to achieve the maximum control of broadleaf weeds.

Application rates of about 0.001 to about 1 Kg/Ha are generally employed in postemergence operations; for preemergence applications, rates of about 0.01 to about 10 Kg/Ha are generally employed.

EXAMPLES

The following Examples are presented to illustrate the various aspects of this invention and should not be construed as limitations to the claims.

EXAMPLE 1

Preparation of 3-Amino-4-bromo-1-methyl-pyrazole

A solution of 4.0 g (41 mmol) of 3-amino-1-methyl-pyrazole in 100 mL of methylene chloride was prepared and to this was added dropwise at ambient temperature with stirring 6.6 g (41 mmol) of bromine (until the bromine color persisted). The white solid that formed was collected by filtration, washed with methylene chloride, and then dissolved in water. Sufficient 2.5N aqueous sodium hydroxide was added to the resulting solution to neutralize it and the neutralized mixture was extracted with methylene chloride. The organic extract was dried over magnesium sulfate and the volatiles were removed by evaporation under reduced pressure to obtain 4.3 g (60 percent of theory) of the title compound as tan crystals melting at 97°-98° C.

Elemental Analysis: Calc. for $C_4H_6BrN_3$: %C, 27.3: %H, 3.44; %N, 23.9 Found: %C, 27.3: %H, 3.21: %N, 23.4

$^1$H NMR Spectrum: (δ ppm from TMS) 7.1 (s, 1H) and 3.7 (brs, 5H).

EXAMPLE 2

Preparation of 4-Amino-3-chloro-1-methyl-pyrazole From Ethyl 3-Amino-1-methylpyrazole-4-carboxylate

A. Preparation of Ethyl 3-Chloro-1-methylpyrazole-4-carboxylate

A solution of 41.4 g (267 mmol) of ethyl 3-amino-1-methylpyrazole-4-carboxylate in a mixture of 150 mL of concentrated hydrochloric acid, 50 mL of 85 percent phosphoric acid, and 100 mL of water was prepared and cooled to about 0° C. A solution of 18.6 g (270 mmol) of sodium nitrite in 50 mL of water was added to this dropwise with cooling and stirring. After a short time the reaction mixture was added dropwise with stirring at ambient temperature to a solution of 46.5 g (484 mmol) of cupric sulfate and 60.0 g (1.03 mol) of sodium chloride in 200 mL of water. When the addition was complete, the mixture was heated to 50° C. with stirring for 1 hr. A solid formed. The mixture was extracted with methylene chloride and the extract was washed with water, dried over magnesium sulfate, and concentrated by evaporation under reduced pressure to obtain an impure solid. This was dried and recrystallized from ethanol to obtain 24.8 g of the title compound as a white solid melting at 76°-77° C.

Elemental Analysis: Calc. for $C_7H_9ClN_2O_2$: %C, 44.6; %H, 4.81: %N, 14.9 Found: %C, 45.6: %H, 5.11; %N, 15.4

$^1$H NMR Spectrum: (δ ppm from TMS) 7.8 (s, 1H), 4.26 (q, 2H, J=7.2), 3.83 (s, 3H), and 1.31 (t, 3H, J=7.2).

B. Preparation of 3-Chloro-1-methylpyrazole-4-carboxylic Acid

A mixture of 23.9 g (127 mmol) of ethyl 3-chloro-1-methylpyrazole-4-carboxylate and 10.4 g (260 mmol) of sodium hydroxide in 130 mL of water was prepared and was heated at reflux for 3 hr. The solution that formed was cooled to about 0° C. and neutralized to pH 6.5 with concentrated hydrochloric acid with stirring and the precipitate that formed was recovered by filtration, washed with water, and dried under reduced pressure to obtain 18.1 g (89 percent of theory) of the title compound as a white solid melting at 211°-213° C. (d).

Elemental Analysis: Calc. for $C_5H_5ClN_2O_2$ %C, 37.4: %H, 3.14; %N, 17.5 Found: %C, 37.2; %H, 3.04; %N, 17.5

$^1$H NMR Spectrum: (δ ppm from TMS) 8.28 (s, 1H) and 3.80 (s, 3H).

C. Preparation of 3-Chloro-1-methylpyrazole-4-carboxamide

A solution of 3-chloro-1-methylpyrazole-4-carboxylic acid (7.8 g, 49 mmol) in 25 mL of tetrahydrofuran was prepared and to this was added at ambient temperature 1,1'-carbonyldiimidazole (7.9 g, 49 mmol). The resulting mixture was stirred at ambient temperature for 8 hr and then 25 mL of ammonium hydroxide was added and the mixture stirred another hour at ambient temperature. The volatile materials were then removed by evaporation under reduced pressure and the residue was dissolved in water. The resulting mixture was extracted with methylene chloride (3×50 mL). The extracts were combined and dried over magnesium sulfate and then concentrated by evaporation under reduced pressure to obtain 5.1 g (65 percent of theory) of the title compound as a white solid melting at 164°-166° C.

Elemental Analysis: Calc. for $C_5H_6ClN_3O$: %C, 37.6; %H, 3.79; %N, 26.3 Found: %C, 38.0: %H, 4.07: %N, 26.0

$^1$H NMR Spectrum: (δ ppm from TMS) 8.17 (s, 1H), 7.28 (bs, 1H), 7.17(bs, 1H), and 3.79 (s, 3H).

D. Preparation of 4-Amino-3-chloro-1-methylpyrazole

A solution of 3-chloro-1-methylpyrazole-4-carboxamide (3.2 g, 20 mmol) in 50 mL of methanol was prepared and cooled to 5° C. and then sodium methoxide (13.5 mL of a 25 percent solution in methanol, 63 mmol) was added with stirring. The resulting clear solution was cooled to 0° C. and bromine (3.2 g, 20 mmol) was added at a rate such that the temperature did not exceed 5° C. The resulting mixture was stirred at ambient temperature for 16 hr and was then heated to reflux for 1 hr. It was then allowed to cool and was concentrated by evaporation under reduced pressure to obtain a white solid. This solid was dissolved in a solution of sodium hydroxide (4.0 g, 0.1 mmol) in 50 mL of methanol and the resulting solution was heated at reflux for 6 hr. The mixture was allowed to cool and was then concentrated by evaporation under reduced pressure. The residue was taken up in 150 mL of a 1:1 mixture of methylene chloride and water and the organic phase was separated, dried over magnesium sulfate, and concentrated by evaporation under reduced pressure to obtain 1.2 g (46 percent of theory) of the title compound as a yellow solid melting at 81°-83° C.

Elemental Analysis: Calc. for $C_4H_6ClN_3$: %C, 36.5: %H, 4.60; %N, 31.9 Found: %C, 36.8: %H, 4.21: %N, 31.6

$^1$H NMR Spectrum: (δ ppm from TMS) 7.22 (s, 1H), 3.64 (s, 3H), and 3.22 (bs, 2H).

EXAMPLE 3

Preparation of N-(4-Bromo-1-methylpyrazol-3-yl)-7-chloro-5-methoxy-1,2,4-triazolo[1,5-c]-pyrimidine-2-sulfonamide Pyridine (1.08 g, 8.0 mmol) and dimethyl sulfoxide (0.2 g) were added to a solution of 7-chloro-5-methoxy-1,2,4-triazolo[1,5-c]pyrimidine-2-sulfonyl chloride (1.0 g, 4.0 mmol) and 3-amino-4-bromo-1-methylpyrazole (0.70 g, 4.0 mmol) in 10 mL of acetonitrile with stirring at ambient temperature and the mixture was allowed to react overnight. The mixture was then concentrated by evaporation under reduced pressure and the residue was taken up in methylene chloride. The resulting solution was extracted with water and dried over magnesium sulfate. The volatile materials were then removed by evaporation under reduced pressure and the solid residue was extracted with diethyl ether and with water, recovered by filtration, and dried under reduced pressure to obtain 0.38 g (25 percent of theory) of the title compound as a white solid melting at 230°-232° C.

Elemental Analysis: Calc. for $C_{10}H_{12}BrClN_7O_3S$: %C, 28.2; %H, 2.84; %N, 23.0 Found: %C, 28.0: %H, 2.42; %N, 23.2

$^1$H NMR Spectrum: (δ ppm from TMS) 10.9 (bs, 1H), 7.84 (s, 1H), 7.83 (s, 1H), 4.23 (s, 3H), and 3.66 (s, 3H).

Additional compounds prepared by this method are given in Table 1.

TABLE 1

N-PYRAZOLYL-1,2,4-TRIAZOLO[1,5-c]PYRIMIDINE-2-SULFONAMIDES

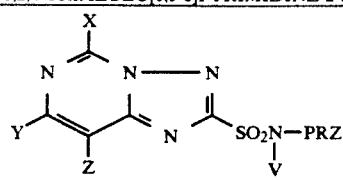

| CPD. NO. | X | Y | Z | V | 3-, 4-, or 5- PRZ | PRZ SUBSTITUENTS | YIELD, % OF THEORY Ex. 3 Method | APPEARANCE | MELTING POINT, °C. | ELEM. ANAL. CALC./FOUND C | H | N |
|---|---|---|---|---|---|---|---|---|---|---|---|---|
| 1 | $OCH_3$ | Cl | H | H | 3- | 1-$CH_3$ | — | white solid | 185–187 | 34.9 / 34.8 | 2.93 / 2.74 | 28.5 / 28.1 |
| 2 | $OCH_3$ | Cl | H | H | 3- | 1-$CH_3$, 4-Br | 25 | pink solid | 230–232 | 28.2 / 28.0 | 2.84 / 2.42 | 23.0 / 23.2 |
| 3 | $OCH_3$ | Cl | H | H | 3- | 1-$CH_3$, 4-$CO_2CH_3$ | 16 | tan solid | 158–160 | 36.9 / 36.9 | 3.01 / 3.28 | 21.4 / 21.8 |
| 4 | $OCH_3$ | $CH_3$ | H | H | 3- | 1-$CH_3$, 4-Br | 40 | pink solid | 191–193 | 32.9 / 32.8 | 3.01 / 2.86 | 24.4 / 24.3 |
| 5 | $OCH_3$ | H | Cl | H | 5- | 1-$CH_3$, 4-Br | 48 | tan solid | 210–212 | 28.4 / 28.2 | 2.15 / 2.30 | 23.2 / 23.9 |
| 6 | $OCH_3$ | H | $CH_3$ | H | 5- | 1-$CH_3$, 4-Br | 98 | tan solid | 207–209 | 32.9 / 32.8 | 3.01 / 3.00 | 24.4 / 24.5 |
| 7 | $OCH_3$ | H | Cl | H | 4- | 1-$CH_3$, 3-$NO_2$ | 44 | tan solid | 120–122 | 30.9 / 31.0 | 2.33 / 2.10 | 28.8 / 29.0 |
| 8 | $OCH_3$ | H | Br | H | 5- | 1-$CH_3$, 4-Br | 56 | tan solid | 221–222 | 25.7 / 25.8 | 1.94 / 1.86 | 21.0 / 21.2 |
| 9 | $OC_2H_5$ | F | H | H | 5- | 1-$CH_3$, 4-Br | 30 | tan solid | 220–221 | 31.4 / 31.3 | 2.64 / 2.49 | 23.3 / 23.5 |
| 10 | $OC_2H_5$ | F | H | H | 4- | 1,5-di$CH_3$, 3-$CF_3$ | 66 | tan solid | 196–198 | 36.9 / 37.2 | 3.10 / 3.05 | 23.2 / 22.9 |
| 11 | $OC_2H_5$ | F | H | H | 3- | 1-$CH_3$, 4-Br | 33 | tan solid | 220–221 (d) | 31. / 31.5 | 2.64 / 2.50 | 23.3 / 23.6 |
| 12 | $OCH_3$ | H | Br | H | 3- | 1-$CH_3$, 4-Br | 60 | tan solid | 204–206 (d) | 25.7 / 25.4 | 1.94 / 1.87 | 21.0 / 21.2 |
| 13 | $OCH_3$ | Cl | H | H | 4- | 1,5-di$CH_3$, 3-$CF_3$ | 31 | tan solid | 224–225 | 30.0 / 30.2 | 2.29 / 2.20 | 20.5 / 20.6 |
| 14 | $OCH_3$ | H | F | H | 3- | 1-$CH_3$, 4-Br | 95 | white solid | 191–193 | 29.6 / 29.4 | 2.23 / 2.17 | 24.1 / 24.1 |
| 15 | $OCH_3$ | H | Cl | H | 3- | 1-$CH_3$, 4-Br | 41 | pink solid | 201–203 | 28.4 / 28.5 | 2.15 / 2.12 | 23.2 / 23.2 |
| 16 | $OCH_3$ | H | $CH_3$ | H | 3- | 1-$CH_3$, 4-Br | 39 | white solid | 210–212 | 32.9 / 32.7 | 3.01 / 2.85 | 24.4 / 24.4 |
| 17 | $OCH_3$ | $C_2H_5$ | H | H | 5- | 1-$CH_3$, 4-Br | 25 | white solid | 192–194 | 34.6 / 34.7 | 3.39 / 3.28 | 23.5 / 23.9 |
| 18 | $OCH_3$ | H | Cl | H | 3- | 1-$CH_3$, 4-I | 49 | white solid | 201–203 | 25.6 / 26.0 | 1.93 / 1.92 | 20.9 / 21.0 |
| 19 | $OC_2H_5$ | F | H | H | 3- | 1-$CH_3$, 4-I | 48 | white solid | 217–218 (d) | 28.3 / 28.3 | 2.37 / 2.28 | 21.0 / 21.0 |
| 20 | $OC_2H_5$ | H | $CH_3$ | H | 3- | 1-$CH_3$, 4-Br | 44 | white solid | 220–222 (d) | 34.6 / 34.2 | 3.39 / 3.29 | 23.6 / 23.8 |
| 21 | $OCH_3$ | Cl | H | H | 3- | 1-$CH_3$, 4-I | 51 | tan solid | 193–184 (d) | 25.6 / 25.7 | 1.93 / 1.73 | 20.9 / 21.1 |
| 22 | $OCH_3$ | H | $OCH_3$ | H | 3- | 1-$CH_3$, 4-Br | 31 | white solid | 209–211 (d) | 31.6 / 31.7 | 2.89 / 2.71 | 23.4 / 23.5 |
| 23 | $OC_2H_5$ | H | H | H | 3- | 1-$CH_3$, 4-Br | 29 | white solid | 230–232 | 32.9 / 32.7 | 3.01 / 2.87 | 24.8 / 24.5 |
| 24 | $OC_2H_5$ | H | H | H | 3- | 1-$CH_3$, 4-I | 37 | white solid | 232–234 | 28.3 / 28.3 | 3.02 / 3.46 | 21.0 / 20.6 |
| 25 | $OCH_3$ | I | H | H | 3- | 1-$CH_3$, 4-Br | 28 | tan solid | 259–261 | 23.4 / 23.5 | 1.76 / 1.99 | 19.1 / 19.3 |
| 26 | $OCH_3$ | I | H | H | 3- | 1-$CH_3$, 4-I | 20 | tan solid | 217–219 | 21.4 / 21.1 | 1.62 / 1.47 | 17.5 / 17.5 |
| 27 | $OCH_3$ | H | I | H | 3- | 1-$CH_3$, 4-Br | 42 | white solid | 233–235 | 23.4 / 23.4 | 1.76 / 1.98 | 19.1 / 18.8 |
| 28 | $OC_2H_5$ | H | $OCH_3$ | H | 3- | 1-$CH_3$, 4-Br | 54 | white solid | 223–225 | 33.3 / 32.9 | 3.26 / 3.45 | 22.7 / 22.2 |
| 29 | $OC_2H_5$ | $CH_3$ | H | H | 3- | 1-$CH_3$, 4-Br | 18 | white solid | 223–225 | 34.6 / 34.3 | 3.39 / 3.38 | 23.6 / 23.1 |
| 30 | $OC_2H_5$ | F | H | H | 5- | 1-(2-pyridinyl), 4-Br | 35 | white solid | 204–206 | 37.3 / 37.3 | 2.50 / 2.54 | 23.2 / 23.5 |
| 31 | $OCH_3$ | H | Cl | H | 5- | 1-$C_6H_5$, 4-Br | 26 | white solid | 240–242 | 39.9 / 40.0 | 2.72 / 2.72 | 20.3 / 20.3 |
| 32 | $OC_2H_5$ | I | H | H | 4- | 1,3-di$CH_3$, 5-$CO_2C_2H_5$ | | | | | | |
| 33 | $OCH_3$ | $CH_2O-CH_3$ | H | H | 4- | 1,3-di$CH_3$, 5-$CO_2C_2H_5$ | | | | | | |

TABLE 1-continued

N-PYRAZOLYL-1,2,4-TRIAZOLO[1,5-c]PYRIMIDINE-2-SULFONAMIDES $$\begin{array}{c} X \\ | \\ N \overset{}{\underset{}{\diagup}} N \text{---} N \\ Y \overset{}{\underset{}{\diagdown}} \text{---} N \overset{\parallel}{\diagdown} SO_2N\text{---}PRZ \\ Z \quad\quad\quad V \end{array}$$

| CPD. NO. | X | Y | Z | V | 3-, 4-, or 5- PRZ | PRZ SUBSTITUENTS | YIELD, % OF THEORY Ex. 3 Method | APPEAR- ANCE | MELTING POINT, °C. | ELEM. ANAL. CALC./FOUND C H N |
|---|---|---|---|---|---|---|---|---|---|---|
| 34 | $OC_2H_5$ | $CH_3$ | H | H | 3- | 1-$CH_3$, 4-I | | | | |
| 35 | $OCH_3$ | H | Cl | H | 5- | 1-$CH_3$, 4-I | | | | |
| 36 | $OCH_3$ | H | Cl | H | 5- | 1,3-di$CH_3$, 4-$CO_2C_2H_5$ | | | | |
| 37 | $OCH_3$ | H | Cl | H | 4- | 1-$CH_3$, 3-Cl | | | | |
| 38 | $OC_2H_5$ | F | H | H | 4- | 1-$CH_3$, 3-Cl | | | | |
| 39 | $OC_2H_5$ | F | H | H | 3- | 1-$CH_3$, 4-Cl | | | | |
| 40 | $OCH_3$ | $CH_3$ | H | H | 5- | 1-$CH_3$, 4-Cl | | | | |
| 41 | $SCH_3$ | Cl | $OC_2H_5$ | $COC_3H_7$ | 5- | 1-$CH_3$, 4-$NO_2$ | | | | |
| 42 | $OCH_3$ | $CHF_2$ | H | $COCH_3$ | 3- | 1-$CH_3$, 4-F | | | | |
| 43 | $OCH_3$ | H | $CF_3$ | $COC_2H_5$ | 3- | 1-$CH_3$, 4-Cl | | | | |
| 44 | $OCH_3$ | H | $OCH_3$ | H | 3- | 1-(4-$C_6H_4Cl$) 5-Cl | | | | |
| 45 | H | $OCH_3$ | F | $COCH_3$ | 4- | 1-$COCH_3$, 3,5-diBr | | | | |
| 46 | $OC_3H_7$ | F | $CH_2F$ | $COCF_3$ | 5- | 1-$CH_3$, 4-F | | | | |
| 47 | $OC_2H_5$ | F | i-$C_3H_7$ | $COCH_3$ | 3- | 1-$CH_3$, 4-$CF_3$ | | | | |
| 48 | $OCH_3$ | H | $OC_2H_5$ | H | 3- | 1-$CH_3$, 4-Br | | | | |

EXAMPLE 4

Preparation of N-(1-Methylpyrazol-3-yl)-7-chloro-5-methoxy-1,2,4-triazolo[1,5-c]pyrimidine-2-sulfonamide Sodium iodide (3.6 g, 24 mmol) and trimethylsilyl chloride 92.6 g, 24 mmol) were added to a solution of 3-amino-1-methylpyrazole (2.3 g, 24 mmol) and triethylamine (2.5 g, 25 mmol) in 20 mL of acetonitrile at ambient temperature with stirring and under dry nitrogen. The mixture was allowed to react until the 3-amino-1-methylpyrazole was essentially all consumed as determined by gas-liquid chromatography. The solvent was then removed by evaporation under reduced pressure and the residue was taken up in diethyl ether. The resulting mixture was filtered to remove solids and the ether was removed by evaporation under reduced pressure. The residue was dissolved in 10 mL of acetonitrile and the resulting solution was combined with 7-chloro-5-methoxy-1,2,4-triazolo[1,5-c]-pyrimidine-2-sulfonyl chloride (2.0 g, 7.0 mmol) and to this was added with stirring at ambient temperature about 0.2 mL of dimethyl sulfoxide catalyst. The resulting mixture was allowed to react for 24 hours and was then concentrated under reduced pressure and the residue was diluted with first water and then methylene chloride. The organic layer was recovered, dried over magnesium sulfate, and concentrated by evaporation under reduced pressure to obtain the title compound as a white solid, which, after drying, amounted to 2.4 g (98 percent of theory) and melted at 185°–187° C.

Elemental Analysis: Calc. for $C_{10}H_{10}ClN_7O_3S$: %C, 34.9: %H, 2.93; %N, 28.5 Found: %C, 34.8: %H, 2.74; %N, 28.1

$^1$H NMR Spectrum: (δ ppm from TMS(DMSO)): 7.82 (s, 1H), 7.50 (s, 1H, J=2.0), 5.90 (d, 1H, J=2.0), 4.24 (s, 3H), and 3.68 (s, 3H).

EXAMPLE 5

Evaluation of Postemergence Herbicidal Activity

Seeds of the desired test plant species were planted in sandy soil having a pH range of about 5–7.5 and an organic matter content of less than 0.5 percent in plastic pots with a surface area of 64 square cm. The plants were grown for 7–20 days in a greenhouse with an approximately 14 hr photoperiod maintained at about 25°–33° C. during the day and 15°–20° C. during the night. Nutrients were added on a regular basis and supplemental lighting was provided with an overhead 1000 Watt multi-vapor lamp when necessary. The plants were employed for testing after they reached the first or second true leaf-stage.

A weighed amount of each test compound in a 10 mL glass vial was dissolved in 4 mL of a 97:3 mixture of acetone and dimethyl sulfoxide to obtain concentrated stock solutions. If the test compound did not dissolve readily, the mixture was warmed and sonicated. The stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration was sprayed evenly onto the various test plants using a Cornwall ™ glass syringe fitted with a TeeJet ™ TN-3 hollow cone nozzle so as to obtain thorough coverage of each plant. Control plants were sprayed in the same manner with the aqueous mixture.

In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent, where 0 corresponds to no injury and 100 corresponds to complete kill. Some of the compounds tested, application rates employed, plant species tested, and results are given in Table 2.

were prepared by dilution of appropriate smaller portions of the stock solution. A 2.5 mL aliquot of each solution of known concentration was sprayed evenly onto the soil of the seeded pots using a Cornwall TM glass syringe fitted with a TeeJet TM TN-3 hollow cone nozzle so as to obtain an even coverage. Control pots were sprayed in the same manner with the aqueous mixture.

The treated pots and control pots were placed in a greenhouse as described above and watered by top-irrigation. After 3 weeks the condition of the test plants as compared with that of the untreated plants was deter-

TABLE 2

| | | | | | | | | | | Wild | Giant | John- | | Barn- |
|---|---|---|---|---|---|---|---|---|---|---|---|---|---|---|
| Cpd. No. | Rate, ppm | Cockle-bur | Jimson-weed | Lambs-quarter | Morning Glory | Pig-weed | Velvet-leaf | Veron-ica | | Buck-wheat | Fox-tail | son-grass | Wild Oats | yard grass |
| 1 | 500 | 60 | 80 | — | 85 | 80 | 95 | — | | 83 | 70 | 83 | 90 | 75 |
| 2 | 7.8 | 90 | 60 | — | 90 | 100 | 90 | — | | 70 | 0 | 100 | 100 | 60 |
| 3 | 63 | 100 | 75 | — | 70 | 80 | 80 | — | | 93 | 65 | 90 | 90 | 85 |
| 4 | 3.9 | 100 | 80 | — | 90 | 100 | 80 | — | | 75 | 60 | 90 | 100 | 70 |
| 5 | 16 | 98 | 85 | — | 80 | 70 | 50 | — | | 50 | 25 | 98 | 75 | 70 |
| 6 | 250 | 80 | 80 | 0 | 100 | 98 | 75 | 95 | | 70 | 80 | 80 | 99 | 95 |
| 7 | 1000 | 70 | 70 | 0 | 0 | 60 | 60 | 40 | | 60 | 20 | 25 | 70 | 30 |
| 8 | 32 | 80 | 85 | 80 | 100 | 100 | 98 | — | | 90 | 45 | 98 | 98 | 80 |
| 9 | 32 | 80 | 80 | 80 | 100 | 40 | 98 | — | | 85 | 40 | 80 | 95 | 80 |
| 10 | 32 | 60 | 70 | 60 | 70 | 0 | 75 | 0 | | 80 | 40 | 80 | 70 | 80 |
| 11 | 16 | 80 | 80 | 80 | 100 | 50 | 85 | — | | 80 | 0 | 90 | 90 | 50 |
| 12 | 32 | 80 | 80 | 90 | 90 | 80 | 60 | 98 | | 70 | 80 | 98 | 98 | 80 |
| 13 | 125 | 90 | 88 | — | 95 | 65 | 80 | — | | 85 | 90 | 85 | 95 | 70 |
| 14 | 16 | 80 | 85 | — | 85 | 70 | 80 | — | | 70 | 0 | 90 | 60 | 85 |
| 15 | 32 | 90 | 80 | 80 | 100 | 98 | 90 | 98 | | 80 | 75 | 78 | 80 | 80 |
| 16 | 63 | 85 | 88 | — | 90 | 100 | 40 | — | | 100 | 35 | 70 | 90 | 80 |
| 17 | 63 | 100 | 75 | — | 75 | 70 | 100 | — | | 60 | 40 | 75 | 90 | 60 |
| 18 | 31 | 85 | 80 | 98 | 98 | 100 | 90 | — | | 85 | 70 | 90 | 95 | 80 |
| 19 | 31 | 90 | 80 | 98 | 100 | 90 | 90 | — | | 85 | 85 | 0 | 80 | 80 |
| 20 | 32 | 70 | 80 | 80 | 80 | 50 | 70 | 60 | | 0 | 0 | 0 | 80 | 80 |
| 21 | 31 | 85 | 75 | 80 | — | 100 | 100 | 100 | | 100 | 20 | 90 | 70 | 90 |
| 22 | 31 | 90 | 85 | 90 | 80 | 100 | 75 | 100 | | 50 | 100 | 90 | 100 | 88 |
| 23 | 16 | 75 | 75 | 95 | 100 | 100 | 90 | 65 | | 95 | 45 | 80 | 75 | 75 |
| 24 | 31 | 70 | 65 | 100 | 80 | 100 | 80 | 75 | | 95 | 25 | 85 | 90 | 80 |
| 25 | 125 | 95 | 85 | 80 | 65 | 100 | 75 | 80 | | 95 | 50 | 85 | 85 | 80 |
| 26 | 63 | 90 | 85 | 50 | 80 | 90 | 50 | 65 | | 90 | 75 | 75 | 100 | 30 |
| 27 | 31 | 85 | 90 | 88 | 100 | 100 | 80 | 90 | | 85 | 100 | 88 | 88 | 80 |
| 28 | 125 | 75 | 65 | 85 | 50 | 95 | 85 | 95 | | 50 | 65 | 85 | 95 | 85 |
| 29 | 16 | 100 | 100 | 90 | 90 | 95 | 95 | 100 | | 90 | 15 | 95 | 95 | 85 |
| 30 | 500 | 100 | 85 | 80 | 90 | 0 | 90 | 50 | | 70 | 60 | 88 | 15 | 85 |
| 31 | 500 | 20 | 85 | 0 | 70 | 0 | 35 | 0 | | 0 | 40 | 28 | 0 | 40 |

EXAMPLE 6

Evaluation of Preemergence Herbicidal Activity

Seeds of the desired test plant species were planted in sandy soil having a pH range of about 5-7.5 and an organic matter content of less than 1.0 percent in plastic pots with a surface area of 103 square cm. The pots were maintained in a greenhouse with an approximately 14 hr photoperiod maintained at about 25°-33° C. during the day and 15°-20° C. during the night. Nutrients were added on a regular basis and supplemental lighting was provided with an overhead 1000 Watt multi-vapor lamp when necessary.

A weighed amount of each test compound in a 10 mL glass vial was dissolved in 8 mL of a 97:3 mixture of acetone and dimethyl sulfoxide to obtain concentrated stock solutions. If the test compound did not dissolve readily, the mixture was warmed and sonicated. The stock solutions obtained were diluted with a 99.9:0.1 mixture of water and Tween TM 20 to obtain application solutions of known concentration. The solutions containing the highest concentration to be tested were prepared by diluting 4 mL aliquots of the stock solution with 8.5 mL of the mixture and lower concentrations mined visually and scored on a scale of 0 to 100 percent, where 0 corresponds to no injury and 100 corresponds to complete kill. Some of the compounds tested, application rates employed, plant species tested, and results are given in Table 3.

TABLE 3

| PREMERGENCE ACTIVITY, PERCENT CONTROL | | | | | | | |
|---|---|---|---|---|---|---|---|
| Cpd. No. | Rate, Kg/Ha | Morn-ing Glory | Pig-weed | Velvet Leaf | Wild Buck-wheat | Barn-yard grass | John-son-grass |
| 4 | 0.28 | 0 | 75 | 75 | — | 85 | 85 |
| 5 | 0.07 | 20 | 100 | 30 | 100 | 70 | 100 |
| 6 | 0.14 | — | — | 35 | 100 | 50 | 35 |
| 8 | 0.14 | 0 | 100 | 60 | 85 | 80 | 95 |
| 9 | 0.14 | 85 | 95 | 90 | 100 | 85 | 95 |
| 10 | 0.28 | 75 | 95 | 90 | — | 80 | 95 |
| 11 | 0.14 | 70 | — | 65 | — | 80 | 85 |
| 12 | 0.14 | 0 | 100 | 55 | 85 | 75 | 90 |
| 15 | 0.07 | 70 | 100 | 45 | 50 | 60 | 100 |
| 16 | 0.14 | 0 | — | 25 | 35 | 0 | 30 |
| 17 | 0.14 | 25 | 85 | 70 | — | 35 | 85 |
| 18 | 0.14 | 85 | 90 | 65 | — | 85 | 95 |
| 19 | 0.14 | 80 | — | 65 | — | 85 | 100 |
| 21 | 0.14 | 70 | 100 | 90 | 90 | 75 | 90 |
| 22 | 0.14 | 70 | 85 | 90 | 70 | 70 | — |
| 25 | 0.14 | 10 | 99 | 20 | 50 | 20 | 90 |

TABLE 3-continued

| | | PREMERGENCE ACTIVITY, PERCENT CONTROL | | | | | |
|---|---|---|---|---|---|---|---|
| Cpd. No. | Rate, Kg/Ha | Morning Glory | Pigweed | Velvet Leaf | Wild Buckwheat | Barnyard grass | Johnsongrass |
| 26 | 0.14 | 20 | 90 | 10 | 10 | 50 | 70 |
| 27 | 0.14 | 70 | 95 | 85 | 90 | 90 | 90 |

EXAMPLE 7

Evaluation of Herbicidal Activity in Transplanted Paddy Rice

The weeds to be tested were planted in plastic containers having known area and allowed to germinate and grow in a greenhouse to the first true leaf stage. Rice (Oryza sativa) plants were grown under greenhouse conditions to the 2.5 leaf stage and were then root-pruned and transplanted into different plastic containers having a known area. Two hills of 3 rice plants each were planted in each container. The rice was then allowed to grow to the 3.5 leaf stage in a greenhouse. Sufficient flood water was added just before treatment to give 3 cm of paddy water.

A weighed amount of each test compound was dissolved in 20 mL of acetone and the resulting solution was diluted with 20 mL of water containing 0.1 percent Tween ™ 20 surfactant to obtain stock mixtures. Measured aliquots of each stock mixture were injected into the water of the plastic containers to give the desired application rates. Untreated containers and containers treated with blank acetone/aqueous Tween ™ 20 surfactant mixture were employed as controls. After treatment the containers were placed in a greenhouse under favorable growing conditions. They were held for 2 days without the addition of flood water and then were watered as needed with deionized water. After 3-4 weeks the condition of the test plants as compared with that of the untreated plants was determined visually and scored on a scale of 0 to 100 percent, where 0 corresponds to no injury and 100 corresponds to complete kill. Some of the compounds tested, application rates employed, plant species tested, and results are given in Table 4.

TABLE 4

| | | PADDY ACTIVITY, PERCENT CONTROL | | | |
|---|---|---|---|---|---|
| Cpd. No. | Rate, G/Ha | Echinochloa crus-galli | Monochloria vaginalis | Scirpus juncoides | Oryza sativa (Rice) |
| 2 | 31 | 50 | 60 | 40 | 5 |
| 4 | 31 | 95 | 100 | 70 | 0 |
| 6 | 125 | 50 | 85 | 55 | 10 |
| 8 | 7.8 | 25 | 80 | 25 | 5 |
| 9 | 7.8 | 35 | 95 | — | 5 |
| 12 | 7.8 | 25 | 80 | 25 | 5 |
| 14 | 16 | 45 | 85 | 50 | 20 |
| 16 | 125 | 95 | 90 | 65 | 5 |
| 17 | 250 | 95 | 75 | 60 | 5 |
| 18 | 8.0 | 30 | 85 | — | 20 |
| 21 | 125 | 100 | 90 | 75 | 35 |
| 23 | 16 | 40 | 80 | — | 0 |
| 24 | 31 | 35 | 100 | 70 | 20 |
| 29 | 63 | 100 | 90 | 70 | 15 |

What is claimed is:

1. An N-pyrazolyl-1,2,4-triazolo[1,5-c]pyrimidine-2-sulfonamide compound of the formula:

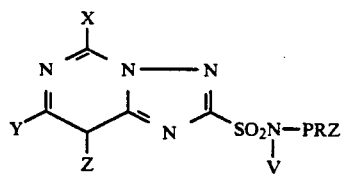

wherein
X represents $OCH_3$ or $OC_2H_5$; and
Y and Z each, independently represent H, $OCH_3$, $OC_2H_5$, $CH_2OCH_3$, $CH_3$, $C_2H_5$, F, Cl, Br, or I;
V represents H or $C(O)R^2$ and when V represents H, the agriculturally acceptable salts thereof;
PRZ represents

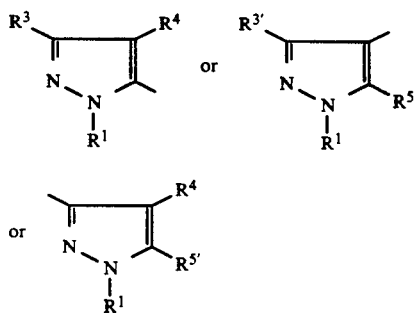

R represents $(C_1-C_3)$alkyl;
$R^1$ represents $CH_3$;
$R^2$ represents $(C_1-C_3)$ alkyl optionally singly to completely substituted with F;
$R^3$ and $R^{5'}$ each independently represent H, $R^2$, F, Cl, Br, or I;
$R^{3'}$ and $R^5$ each independently represent H, $R^2$, F, Cl, Br, I, $NO_2$, $COR^2$, $CO_2R$, or phenyl optionally substituted with up to two substituents selected from $CH_3$, $CF_3$, F, Cl, Br, $OCH_3$, and $SCH_3$; and
$R^4$ represents F, Cl, Br, I, $R^2$, $SR^2$, $NR_2$, $COR^2$, $SO_2R^2$, COphenyl, or phenyl, each phenyl optionally substituted with up to two substituents selected from $CH_3$, $CF_3$, F, Cl, Br, $OCH_3$, and $SCH_3$.

2. A compound according to claim 1 wherein V represents H and the agriculturally acceptable salts thereof.

3. A compound according to claim 1 wherein one of Y and Z represents $OCH_3$, $OC_2H_5$, $CH_3$, F, Cl, Br, or I and the other represents H.

4. A compound according to claim 1 wherein PRZ represents a substituted 3-pyrazolyl moiety.

5. A compound according to claim 4 wherein $R^4$ represents Cl, Br, I, or $CF_3$ and $R^{5'}$ represents H.

6. A compound according to claim 1 wherein PRZ represents a substituted 5-pyrazolyl moiety.

7. A compound according to claim 6 wherein $R^4$ represents Cl, Br, I, or $CF_3$ and $R^3$ represents H.

8. A compound according to claim 1 wherein PRZ represents a substituted 4-pyrazolyl moiety and $R^{3'}$ represents Cl, Br, I, or $CF_3$ and $R^5$ represents H, Cl, Br, I, or $CF_3$.

9. A compound according to claim 3, N-(4-bromo-1-methyl-3-pyrazolyl)-7-chloro-5-methoxy-1,2,4-triazolo[1,5-c]pyrimidine-2-sulfonamide.

10. A compound according to claim 3, N-(4-bromo-1-methyl-3-pyrazolyl)-5-methoxy-7-methyl-1,2,4-triazolo[1,5-c]pyrimidine-2-sulfonamide.

11. A compound according to claim 3, N-(4-bromo-1-methyl-3-pyrazolyl)-8-chloro-5-methoxy-1,2,4-triazolo[1,5-c]pyrimidine-2-sulfonamide.

12. A compound according to claim 3, N-(4-bromo-1-methyl-5-pyrazolyl)-7-fluoro-5-ethoxy-1,2,4-triazolo[1,5-c]pyrimidine-2-sulfonamide.

13. An herbicidal composition comprising an agriculturally acceptable adjuvant or carrier and an herbicidally effective amount of an N-pyrazolyl-1,2,4-triazolo[1,5-c]pyrimidine-2-sulfonamide compound of the formula:

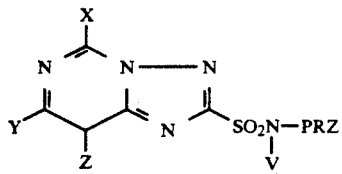

wherein
X represents OCH$_3$ or OC$_2$H$_5$; and
Y and Z each, independently represent H, OCH$_3$, OC$_2$H$_5$, CH$_2$OCH$_3$, CH$_3$, C$_2$H$_5$, F, Cl, Br, or I;
V represents H or C(O)R$^2$ and when V represents H, the agriculturally acceptable salts thereof;
PRZ represents

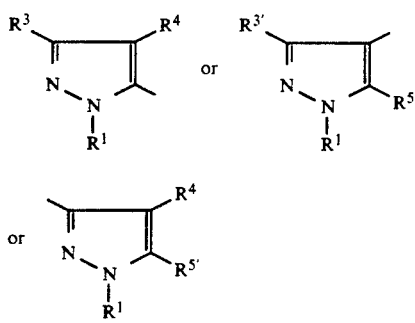

R represents (C$_1$-C$_3$)alkyl;
R$^1$ represents CH$_3$;
R$^2$ represents (C$_1$-C$_3$)alkyl optionally singly to completely substituted with F;
R$^3$ and R$^{5'}$ each independently represent H, R$^2$, F, Cl, Br, or I;
R$^{3'}$ and R$^5$ each independently represent H, R$^2$, F, Cl, Br, I, NO$_2$, COR$^2$, CO$_2$R, or phenyl optionally substituted with up to two substituents selected from CH$_3$, CF$_3$, F, Cl, Br, OCH$_3$, and SCH$_3$; and
R$^4$ represents F, Cl, Br, I, R$^2$, SR$^2$, NR$_2$, COR$^2$, SO$_2$R$^2$, COphenyl, or phenyl, each phenyl optionally substituted with up to two substituents selected from CH$_3$, CF$_3$, F, Cl, Br, OCH$_3$, and SCH$_3$.

14. A composition according to claim 13 wherein V represents H and the agriculturally acceptable salts thereof.

15. A composition according to claim 13 wherein one of Y and Z represents OCH$_3$, OC$_2$H$_5$, CH$_3$, F, Cl, Br, or I and the other represents H.

16. A composition according to claim 13 wherein PRZ represents a substituted 3-pyrazolyl moiety.

17. A composition according to claim 16 wherein R$^4$ represents Cl, Br, I, or CF$_3$ and R$^{5'}$ represents H.

18. A composition according to claim 13 wherein PRZ represents a substituted 5-pyrazolyl moiety.

19. A composition according to claim 18 wherein R$^4$ represents Cl, Br, I, or CF$_3$ and R$^3$ represents H.

20. A composition according to claim 1 wherein PRZ represents a substituted 4-pyrazolyl moiety and R$^{3'}$ represents Cl, Br, I, or CF$_3$ and R$^5$ represents H, Cl, Br, I, or CF$_3$.

21. A composition according to claim 15 wherein the compound is N-(4-bromo-1-methyl-3-pyrazolyl)-7-chloro-5-methoxy-1,2,4-triazolo[1,5-c]-pyrimidine-2-sulfonamide.

22. A composition according to claim 15 wherein the compound is N-(4-bromo-1-methyl-3-pyrazolyl)-5-methoxy-7-methyl-1,2,4-triazolo[1,5-c]-pyrimidine-2-sulfonamide.

23. A composition according to claim 15, wherein the compound is N-(4-bromo-1-methyl-3-pyrazolyl)-8-chloro-5-methoxy-1,2,4-triazolo[1,5-c]-pyrimidine-2-sulfonamide.

24. A composition according to claim 15 wherein the compound is N-(4-bromo-1-methyl-5-pyrazolyl)-7-fluoro-5-ethoxy-1,2,4-triazolo[1,5-c]-pyrimidine-2-sulfonamide.

25. A method of controlling unwanted vegetation which comprises applying to the vegetation or to the locus of the vegetation an herbicidally effective amount an N-pyrazolyl-1,2,4-triazolo[1,5-c]pyrimidine-2-sulfonamide compound of the formula:

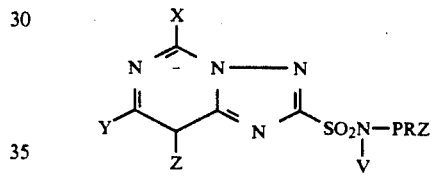

wherein
X represents OCH$_3$ or OC$_2$H$_5$; and
Y and Z each, independently represent H, OCH$_3$, OC$_2$H$_5$, CH$_2$OCH$_3$, CH$_3$, C$_2$H$_5$, F, Cl, Br, or I;
V represents H or C(O)R$^2$ and when V represents H, the agriculturally acceptable salts thereof;
PRZ represents

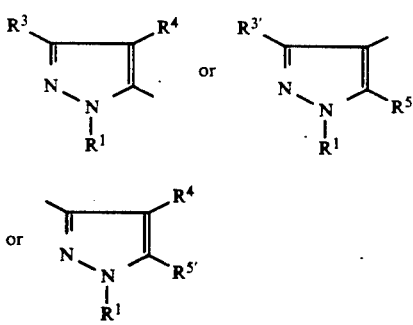

R represents (C$_1$-C$_3$)alkyl;
R$^1$ represents CH$_3$;
R$^2$ represents (C$_1$-C$_3$)alkyl optionally singly to completely substituted with F;
R$^3$ and R$^{5'}$ each independently represent H, R$^2$, F, Cl, Br, or I;
R$^{3'}$ and R$^5$ each independently represent H, R$^2$, F, Cl, Br, I, NO$_2$, COR$^2$, CO$_2$R, or phenyl optionally substituted with up to two substituents selected from CH$_3$, CF$_3$, F, Cl, Br, OCH$_3$, and SCH$_3$; and $R^4$ represents F, Cl, Br, I, $R^2$, $SR^2$, $NR_2$, $COR^2$, $SO_2R^2$, COphenyl, or phenyl, each phenyl optionally substituted with up to two substituents selected from $CH_3$, $CF_3$, F, Cl, Br, $OCH_3$, and $SCH_3$.

26. A method according to claim 25 wherein V represents H and the agriculturally acceptable salts thereof.

27. A method according to claim 25 wherein one of Y and Z represents $OCH_3$, $OC_2H_5$, $CH_3$, F, Cl, Br, or I and the other represents H.

28. A method according to claim 25 wherein PRZ represents a substituted 3-pyrazolyl moiety.

29. A method according to claim 28 wherein $R^4$ represents Cl, Br, I, or $CF_3$ and $R^{5'}$ represents H.

30. A method according to claim 13 wherein PRZ represents a substituted 5-pyrazolyl moiety.

31. A method according to claim 30 wherein $R^4$ represents Cl, Br, I, or $CF_3$ and $R^3$ represents H.

32. A method according to claim 13 wherein PRZ represents a substituted 4-pyrazolyl moiety and $R^{3'}$ represents Cl, Br, I, or $CF_3$ and $R^5$ represents H, Cl, Br, I, or $CF_3$.

33. A method according to claim 27 wherein the compound is N-(4-bromo-1-methyl-3-pyrazolyl)-7-chloro-5-methoxy-1,2,4-triazolo[1,5-c]pyrimidine-2-sulfonamide.

34. A method according to claim 27 wherein the compound is N-(4-bromo-1-methyl-3-pyrazolyl)-5-methoxy-7-methyl-1,2,4-triazolo[1,5-c]pyrimidine-2-sulfonamide.

35. A method according to claim 27, wherein the compound is N-(4-bromo-1-methyl-3-pyrazolyl)-8-chloro-5-methoxy-1,2,4-triazolo[1,5-c]pyrimidine-2-sulfonamide.

36. A method according to claim 27 wherein the compound is N-(4-bromo-1-methyl-5-pyrazolyl)-7-fluoro-5-ethoxy-1,2,4-triazolo[1,5-c]pyrimidine-2-sulfonamide.

37. A method according to claim 25 wherein the compound is applied postemergently.

38. A method according to claim 25 wherein an N-pyrazolyl-1,2,4-triazolo[1,5-c]pyrimidine-2-sulfonamide compound of the formula given wherein $R^3$, $R^{3'}$, $R^5$, and $R^{5'}$ each independently represent H, F, Cl, Br, or I and $R^4$ represents F, Cl, Br, or I is applied in a selectively effective amount to paddy rice.

39. A method according to claim 25 wherein an N-pyrazolyl-1,2,4-triazolo[1,5-c]pyrimidine-2-sulfonamide compound of the formula given wherein Y represents $CH_3$ or $C_2H_5$ and Z represents H is applied in a selectively effective amount to paddy rice.

40. A method according to claim 39 wherein the compound is N-(4-bromo-1-methylpyrazol-3-yl)-7-methyl-5-methoxy-1,2,4-triazolo[1,5-c]pyrimidine-2-sulfonamide or N-(4-bromo-1-methylpyrazol-3-yl)-7-methyl-5-ethoxy-1,2,4-triazolo[1,5-c]pyrimidine-2-sulfonamide.

* * * * *